United States Patent [19]

Thompson

[11] 4,186,373
[45] Jan. 29, 1980

[54] SYSTEM FOR MEASURING IN SITU ACOUSTIC ENERGY PROPERTIES OF OCEAN FLOOR SOILS

[75] Inventor: John R. Thompson, Camarillo, Calif.

[73] Assignee: The United States of America as represented by the Secretary of the Navy, Washington, D.C.

[21] Appl. No.: 908,487

[22] Filed: May 22, 1978

[51] Int. Cl.² ........................ G01N 3/30; G01V 1/38
[52] U.S. Cl. .................................... 367/131; 73/599; 181/108; 181/139; 367/15
[58] Field of Search ............... 340/3 A, 5 C, 5 R, 7 R; 73/599, 170 A; 181/108, 139, 140

[56] References Cited

U.S. PATENT DOCUMENTS

| | | | |
|---|---|---|---|
| 3,154,170 | 10/1964 | Noiseux | 340/5 C |
| 3,373,400 | 3/1968 | Epstein et al. | 340/5 R |
| 3,555,499 | 1/1971 | MacDonald et al. | 73/170 A |
| 3,561,268 | 2/1971 | Massa | 340/5 R |
| 3,859,598 | 1/1975 | McElwain et al. | 340/17 |
| 3,901,075 | 8/1975 | Hampton et al. | 73/153 |
| 4,007,633 | 2/1977 | Thompson | 340/3 A |

FOREIGN PATENT DOCUMENTS 453629  12/1974  U.S.S.R. ................................ 73/599

*Primary Examiner*—Nelson Moskowitz
*Attorney, Agent, or Firm*—Richard S. Sciascia; Joseph M. St. Amand; Darrell E. Hollis

[57] ABSTRACT

A hollow, projectile-shaped body containing an acoustical transducer is released into the sea such that the body descends in free fall until it strikes and penetrates the sea floor, coming to a rest therein. Acoustic signals emanating from the acoustic transducer are processed to generate a direct current analog signal which is a function of the acoustical attenuation of the acoustic signals from a time immediately preceding the body striking the sea floor surface until the body comes to rest in the sea floor, thereby obtaining an indication of the physical characteristics of the sea floor.

14 Claims, 2 Drawing Figures

SYSTEM FOR MEASURING IN SITU ACOUSTIC ENERGY PROPERTIES OF OCEAN FLOOR SOILS

BACKGROUND OF THE INVENTION

1. Field of the Invention

The present invention relates generally to systems for determining the physical characteristics of a sea floor and, more particularly, to such systems for measuring acoustic attenuation in sea floor soils.

2. Description of the Prior Art

The prior art methods of measuring the acoustic properties of sea floors involved taking core samples, laboriously from surface vessels, returning these core samples to the laboratory and measuring acoustic characteristics of the samples by laboratory modeling methods.

Another prior art method of measuring acoustic properties of sea floors involves placing a pair of probes, (one a transmitter of acoustic energy and the other a receiver of the transmitted acoustic energy) in the ocean floor and measuring the acoustic properties between the two. For example, knowing the distance between the two probes the acoustic attenuation could be reduced to attenuation versus linear unit of measurement.

These prior art methods are costly and time consuming. Additionally, core sampling prior art methods do not permit in-situ measurements.

SUMMARY OF THE INVENTION

The present invention overcomes the disadvantages and limitations of the prior art by providing an improved system for measuring acoustic energy properties of ocean floor soils. The present invention utilizes an acoustical transmitter contained in a free falling penetrometer to transduce and transmit an electrical analog of the desired physical parameters of a sea floor to a surface receiver. The received signals are processed to generate a direct current analog signal which is a function of the acoustical attenuation of the transmitted signals from the time immediately preceding the body striking the sea floor surface until the body comes to rest in the sea floor.

Accordingly, one object of the present invention is to provide a method of determining the physical characteristics of a sea floor.

Another object of the present invention is to provide both physical and electrical integrity.

A still further object of the present invention is to reduce costs while increasing efficiency.

One other object of the present invention is to increase reliability.

A still further object of the present invention is to provide information on the acoustical attenuation properties of sea floor soils.

Other objects and a more complete appreciation of the present invention and its many intended advantages will develop as the same becomes better understood in reference to the following detailed description when considered in connection with the accompanying drawings in which like reference numerals designate like parts throughout the figures thereof and therein.

DETAILED DESCRIPTION OF THE PREFERRED EMBODIMENT

Figure 1:
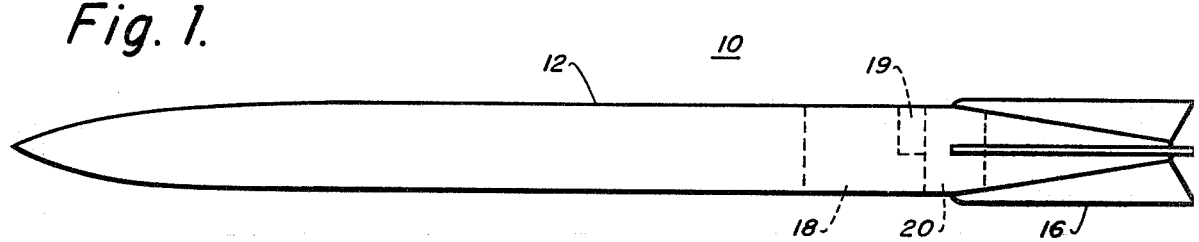
FIG. 1 is a side elevation illustrating a penetrometer utilized in the present invention.

FIG. 1 illustrates a projectile or penetrometer 10. Projectile 10 comprises an elongated body 12 with a known specific size, weight and shape. When released into the sea, body 12 falls freely. Its terminal velocity while in free fall as well as its other physcial dynamics are known quantities.

Fin assembly 16 is attached to the end of body 12. Fin assembly 16 includes four fins for stabilizing body 12 while body 12 is descending toward the sea floor in free fall. Acoustic amplifier and battery power supply section 18, acoustic transducer 20, and timing circuit 19 are contained within body 12. Acoustic transducer 20 emits a constant frequency signal, for example, 12 kilohertz that is directed upward toward the sea surface.

The projectile or penetrometer 10 is released near the surface of the sea and descends in free fall toward the sea floor. Upon striking the sea floor the penetrometer 10 will penetrate into the sea floor and come to rest therein.

Once acoustic transducer 20 penetrates the sea floor, the amplitude of the a-c signal transmitted therefrom as received at the sea surface experiences attenuation with further attenuation occurring as acoustic transducer 20 penetrates further into the sea floor until penetrometer 10 comes to rest therein.

As penetrometer 10 penetrates the sea floor it disturbs the soil adjacent its path of penetration, i.e., creates a hole in the sea floor soil. Since the path of penetrometer 10 is substantially vertical in the sea floor soils and since acoustic transducer 20 directs its signals substantially vertically upwards, the disturbing of the sea floor soil immediately above penetrometer 10 may introduce erroneous indications of the attenuation of the acoustic signal by the sea floor soil. Therefore, a timing circuit 19 has been included within penetrometer 10 to provide data as to the magnitude of the error introduced, if any.

Timing circuit 19 is actuated upon the release of penetrometer 10. It is known that penetrometer 10 will come to rest within the sea floor within approximately five minutes from time of release. Therefore, timing circuit 19 is set to turn acoustic transducer 20 off approximately five minutes after release of penetrometer 10 from the sea surface. Thereafter, timing circuit 19 prevents acoustic transducer 20 from transmitting for a first predetermined time period and then turns transducer 20 on for a second predetermined time period. It is envisioned that the second predetermined time period will be approximately one half hour. The first predetermined time period should be of sufficient duration to allow the disturbed soil to reform. If the attenuation pattern of the signals emitted by acoustic transducer 20 are identical to those recorded earlier then no error was introduced by the soil being disturbed by penetrometer 10. On the other hand, if the attenuation pattern has changed then an error was introduced. The information received indicates the magnitude of the error which is used to eliminate the error in the collected data.

The timing circuit is necessary as there may be several other penetrometers dropped in the vicinity of penetrometer 10. If the acoustic transducer 20 of penetrometer 10 were allowed to transmit indefinitely the signal from transducer 20 would interfere with the signals from the other penetrometers.

Figure 2:
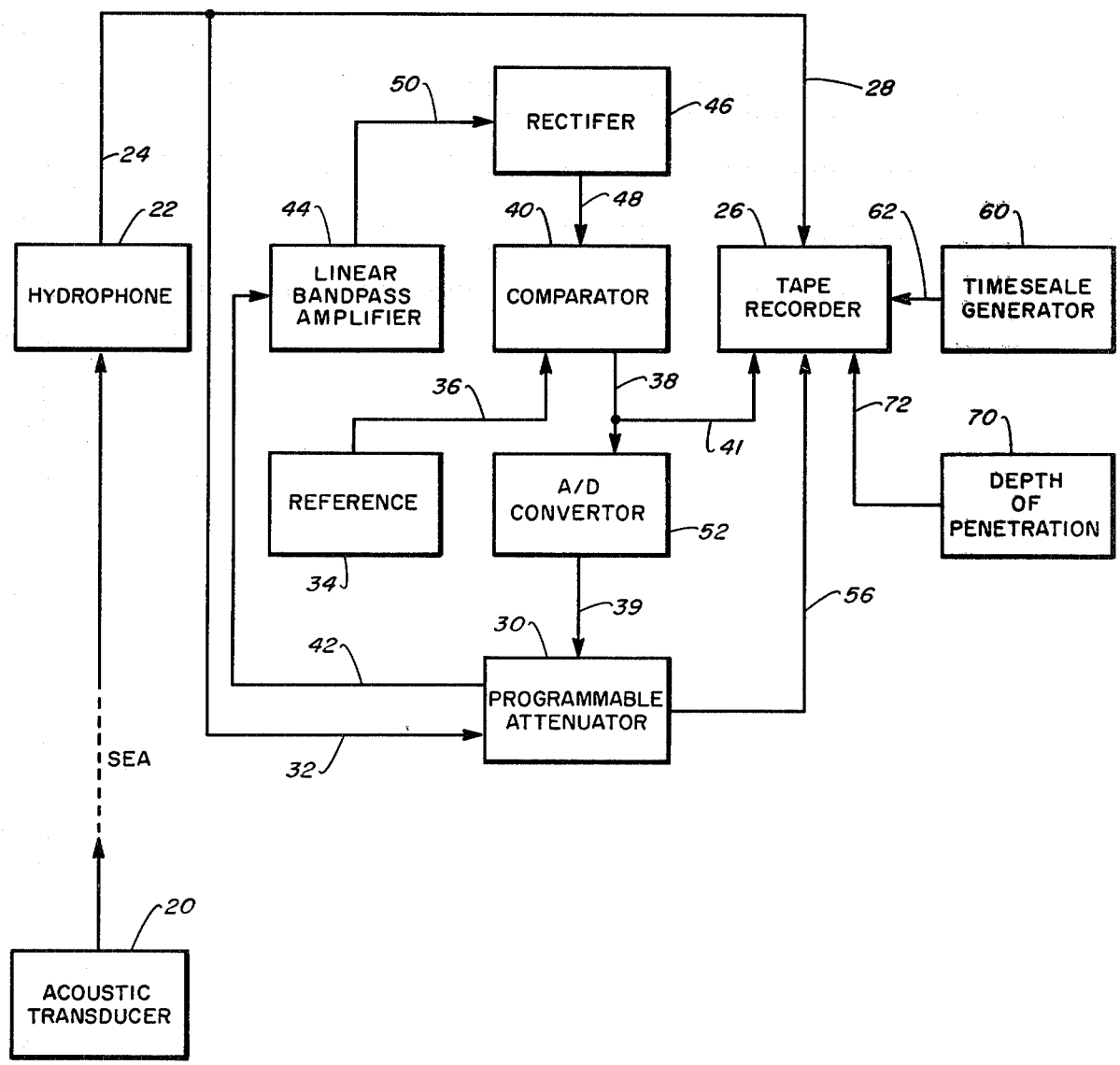
FIG. 2 is a block diagram of the electrical acoustical signal processing equipment in one embodiment of the present invention.

Now turning to FIG. 2 a block diagram of a circuit for processing the a-c signal emitted from acoustic transducer 20 of penetrometer 10 is shown. A hydrophone 22 placed near the surface of the sea receives the a-c signal generated by acoustic transducer 20. Hydrophone 22 transduces this acoustic signal into an electrical a-c signal which appears on line 24. The a-c signal on line 24 is coupled to tape recorder 26 via line 28 and to programmable attenuator 30 via line 32.

The amplitude of the a-c signal on line 42 as represented by the rectified signal on line 48 is compared with a reference signal generated by reference 34 onto line 36. An error signal indicating the difference in amplitude between the reference signal on line 36 and the rectified a-c signal on line 48 is generated on line 38 by comparator 40.

The error signal appearing on line 38 is converted into a digital format by analogs-to-digital converter 52. For compatibility with programmable attenuator 30, the digitized data on line 39 is in binary coded decimal format preferably 40-20-10-8-4-2-1.

It is noted that comparator 40 and analog-to-digital convertor 52 may alternately be replaced in FIG. 2 by an off-the-shelf, differential input, digital voltmeter having the capability of providing a digitized error signal to programmable attenuator 30.

Programmable attenuator 30 in response to the BCD error signal on line 39 controls the a-c signal on line 42 by attenuating the same. This a-c signal appearing on line 42, due to the controlling function of programmable attenuator 30, maintains a constant amplitude, i.e., equal to that of the reference signal on line 36.

The constant amplitude a-c signal on line 42 is amplified by linear band pass amplifier 44 and then rectified by rectifier 46. The output at rectifier 46 on line 48 comprises a d-c signal whose d-c level is a function of the amplitude of the a-c signal entering rectifier 46 from linear band pass amplifier 44 on line 50. The reference signal from reference circuit 34 is coupled to comparator 40 via line 36 for comparison with the d-c signal on line 48 as described supra. The reference signal appearing on line 36 is a d-c voltage of predetermined magnitude. The error signal appearing on line 38 from comparator 40 is digitized by A/D converter 52 and coupled to programmable attenuator 30 which then corrects the amplitude of the a-c signal leaving programmable attenuator 30 via line 42. Thus, the amplitude of the a-c signal on line 42 is set by the d-c reference signal generated by reference circuit 34.

The digital control signal on line 39 is coupled via programmable attenuator 30 to tape recorder 26 via line 56. The signal on line 56 comprises a digital dynamic record of the setting of programmable attenuator 30. Thus, information containing the magnitude of attenuation applied to the signal on line 32 in order to maintain the signal on line 42 at a constant amplitude is contained in the signal on line 56.

Also, the d-c control or error signal on line 38 is coupled to tape recorder 26 via line 41. Thus, a direct-current analog signal (line 41) as well as a digital BCD signal (line 56) which are both functions of the acoustical attenuation of the acoustical signal from acoustic transducer 20 are recorded by tape recorder 26 on separate channels.

Time scale generator 60 generates a time scale signal which is coupled to tape recorder 26 via line 62. Thus, tape recorder 26 records the a-c signal from hydrophone 22, the error signal from comparator 40, and the digital signal from A/D converter 52 on three separate channels within tape recorder 26 simultaneously with the time scale signal from time scale generator 60 being recorded on a fourth channel.

In addition, depth of penetration information is recorded on a fifth channel of tape recorder 26 provided by depth of penetration circuit 70 via line 72. Depth of penetration circuit 70 may be obtained from the teachings of U.S. Pat. No. 4,007,633. The teachings of U.S. Pat. No. 4,007,633 provide for a permanent recording of the apparent frequency change (i.e., doppler) versus time from the moment penetrometer 10 contacts the ocean floor until penetrometer 10 comes to rest therein. Knowing the frequency or doppler change versus time, depth of penetration of penetrometer 10 within sea floor can be established. Thus, a plot of the acoustical attenuation of the signal from acoustical transducer 20 versus depth of penetration of acoustical transducer 20 may be generated.

It is noted that programmable attenuator 30 is a commercially available off-the-shelf device such as General Radio Model 1452 having a dynamic range of approximately 80 db.

It is also noted that linear band pass amplifier 44, rectifier 46, A/D converter 52, comparator 40, and programmable attenuator 30 comprise a closed loop servo system. The output of A/D converter 52 controls programmable attenuator 30 such that the signal on line 42 is maintained at a peak amplitude corresponding to the d-c voltage level of the reference signal on line 36 generated by reference circuit 34.

Thus, the embodiment of FIG. 2 generates a profile of depth versus acoustic attenuation in the sea floor soil. Programmable attenuator 30 is capable of changing attenuation levels at the rate of 2,000 changes per second. Thus, if penetrometer 10 requires approximately 200 miliseconds to come to rest after contact with the ocean floor, 400 changes of attenuation will be generated on line 56 and recorded on tape recorder 26. Based on present assumptions about thirty 1 db increments would establish a penetration versus attenuation profile with a resolution on the depth below the ocean floor axis of an x-y plot of less than one foot.

It is envisioned that by adding additional acoustic measuring devices to penetrometer 10 the speed of sound in the ocean floor may be determined as well as other acoustic characteristics such as phase shift. Also, some requirements may exist for certain ocean floors which require deeper penetration than can be achieved by free falling penetrometer 10. In such cases, additional penetration may be achieved by accelerating penetrometer 10 at an appropriate rate using propellant techniques initiated at the proper time to achieve the required deeper penetration.

Obviously, numerous modifications and variations of the present invention are possible in light of the above teachings. It is therefore to be understood that within the scope of the appended claims the invention may be practiced otherwise than as specifically described herein.

What is claimed is:

1. A method of determining the acoustic energy properties of sea floor soils comprising the steps of:
    a. providing a body of known size, weight and shape capable of transmitting acoustical signals;

b. releasing said body into the sea such that said body descends in free fall until it strikes and penetrates the sea floor coming to rest therein;

c. receiving said transmitted acoustic signals with a receiver disposed near the sea surface; and d. generating an analog signal from the received acoustic signals, said generated signal being a function of the acoustical attenuation of the transmitted acoustic signal from a time immediately preceeding said body's striking the sea floor surface until said body comes to rest in the sea floor.

2. The method of claim 1 comprising the further steps of:

a. terminating the generation and transmission of said acoustical signals after said body comes to rest in the sea floor for a first predetermined time period; and b. resuming the generation and transmission of said acoustical signals for a second predetermined time period following said first predetermined time period whereby data indicating the effect of the soil disturbed by said body penetrating said sea floor is generated.

3. The method of claim 1 comprising the further step of recording said direct-current analog signal.

4. The method of claim 3 comprising the further steps of:

a. generating a time scale signal; and b. recording said time scale signal in conjunction with said direct-current analog signal.

5. The method of claim 4 comprising the further steps of:

a. generating a signal which is a function of the depth of penetration of said body; and b. recording said depth of penetration signal in conjunction with said direct-current analog signal and said time scale signal.

6. The method of claim 1 wherein the step of generating includes generating from the received acoustic signal a digital signal which is a function of the acoustical attenuation of the acoustic signal from a time immediately preceding said body's striking the sea floor surface until said body comes to rest in the sea floor.

7. An apparatus for generating a signal that is a function of the attenuation of an a-c signal comprising:

a. means for providing a first a-c signal;

b. means for providing a reference signal;

c. means responsive to said first a-c signal for generating an error signal, said error signal being a function of the difference in amplitude between said first a-c signal and said reference signal; and d. means responsive to said error signal and said first a-c signal for generating a second a-c signal having an amplitude substantially equal to said reference signal.

8. The apparatus of claim 7 further comprising means for recording said error signal thereby providing a record of the attenuation of said first a-c signal versus time.

9. The apparatus of claim 8 wherein said recording means includes a tape recorder.

10. The apparatus of claim 8 further comprising a time scale generator means communicating with said recording means for recording a time scale in conjunction with the recordation of said error signal.

11. The apparatus of claim 10 further including means for recording said first a-c signal in conjunction with said error signal and said time scale.

12. The apparatus of claim 7 wherein said error signal generating means includes:

a. a bandpass amplifier responsive to said first a-c signal;

b. a rectifier coupled to said bandpass amplifier for generating a d-c signal that is a function of the amplitude of said first a-c signal;

c. a comparator responsive to said reference signal and said d-c signal for generating said error signal; and d. an analog-to-digital converter for converting said error signal into digital format.

13. The apparatus of claim 7 wherein said second a-c signal generating means includes a programmable attenuator.

14. A method of determining the acoustic energy properties of sea floor soils comprising the steps of:

a. providing a body of known size, weight and shape capable of transmitting acoustical signals;

b. releasing said body into the sea such that said body descends in free fall until it strikes and penetrates the sea floor coming to rest therein;

c. receiving said transmitted acoustic signals with a receiver disposed near the sea surface; and d. generating an analog signal from the received acoustic signals, said generated signal being a function of the acoustical attenuation of the transmitted acoustic signal from a time immediately preceeding said body's striking the sea floor surface until said body comes to rest in the sea floor.

e. terminating the transmission of said acoustic signals after said body comes to rest in the sea floor for a first predetermined time period; and f. resuming the transmission of said acoustic signals for a second predetermined time period following said first predetermined time period whereby data indicating the effect of the soil distributed by said body penetrating said sea floor is generated.

* * * * *